United States Patent [19]

Merger et al.

[11] Patent Number: 4,748,226
[45] Date of Patent: May 31, 1988

[54] METHOD OF PREPARATION OF NOVEL 2-(ALKOXYMETHYL)-PENTANE-1,5-DIISOCYANATES, 2-(ALKOXYMETHYL)-PENTANE-1,5-DIURETHANES, AND 2-(ALKOXYMETHYL)-PENTANE-1,5-DICARBAMIC ACID CHLORIDES AND THEIR USES

[75] Inventors: Franz Merger, Frankenthal; Wolfgang Schwarz, Pfinztal, both of Fed. Rep. of Germany

[73] Assignee: BASF Aktiengesellschaft, Ludwigshafen, Fed. Rep. of Germany

[21] Appl. No.: 97,505

[22] Filed: Sep. 16, 1987

[30] Foreign Application Priority Data

Sep. 20, 1986 [DE] Fed. Rep. of Germany ....... 3632010

[51] Int. Cl.$^4$ ............................................. C08G 18/77
[52] U.S. Cl. ......................................... 528/85; 528/68; 560/158; 560/345; 560/357; 564/508
[58] Field of Search .................... 528/85, 68; 560/158, 560/345, 357; 564/508

[56] References Cited

U.S. PATENT DOCUMENTS 3,691,225  9/1972  Kamal et al. .................. 564/508

Primary Examiner—Maurice J. Welsh
Attorney, Agent, or Firm—Bill C. Panagos

[57] ABSTRACT

This invention relates to novel 2-(alkoxymethyl) pentane-1,5-diisocyanates, 2-(alkoxymethyl)-pentane-1,5-diurethanes, and 2-(alkoxymethyl)-pentane 1,5-dicarbamic acid chlorides having the structure:

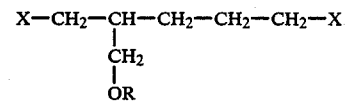

in which R is a straight chain or branched $C_1$–$C_{20}$-alkyl radical, a straight chain or branched $C_2$–$C_{20}$-alkenyl radical, a straight chain or branched $C_3$–$C_{20}$-oxaalkyl radical, an optionally substituted $C_5$–$C_{12}$-cycloalkyl radical, or an optionally substituted $C_7$–$C_{20}$-aralkyl radical and X is a —NCO—, —NH—$CO_2R^1$—, —NH-$CO_2R^2$— OR - NHCOCl-group whereby $R^1$ and $R^2$ can be the same or different and are a straight chain or branched $C_1$–$C_{20}$-alkyl radical or a $C_5$–$C_{12}$ cycloalkyl radical, as well as a process for their preparation. The 2-(alkoxymethyl)-pentane-1,5-diurethanes or 2-(alkoxymethyl)-pentane-1,5-dicarbamic acid chlorides are suited for the preparation of 2-(alkoxymethyl)-pentane-1,5-diisocyanates, which in turn are used for the preparation of plastics using the polyisocyanate addition polymerization process.

14 Claims, No Drawings

METHOD OF PREPARATION OF NOVEL 2-(ALKOXYMETHYL)-PENTANE-1,5-DIISOCYANATES, 2-(ALKOXYMETHYL)-PENTANE-1,5-DIURETHANES, AND 2-(ALKOXYMETHYL)-PENTANE-1,5-DICARBAMIC ACID CHLORIDES AND THEIR USES

BACKGROUND OF THE INVENTION

This invention relates to novel 2-(alkoxymethyl)pentane-1,5-diisocyanates and processes for their preparation and use. This invention further relates to the preparation of plastics via the polyisocyanate addition polymerization process using these novel diisocyanates, as well as 2-(alkoxymethyl)-pentane-1,5-diurethanes and 2-(alkoxymethyl)pentane-1,5-dicarbamic acid chlorides, which are particularly suited as starting components in the preparation of 2-(alkoxymethyl)-pentane-1,5-diisocyanates.

SUMMARY OF THE INVENTION

This invention relates to novel 2-(alkoxymethyl)pentane-1,5-diisocyanates, 2-(alkoxymethyl)-pentane-1,5-diurethanes, and 2-(alkoxymethyl)-pentane 1,5-dicarbamic acid chlorides having the structure:

$$X-CH_2-CH-CH_2-CH_2-CH_2-X$$
$$|$$
$$CH_2$$
$$|$$
$$OR$$

in which R is a straight chain or branched $C_1-C_{20}$-alkyl radical, a straight chain or branched $C_2-C_{20}$-alkenyl radical, a straight chain or branched $C_3-C_{20}$-oxaalkyl radical, an optionally substituted $C_5-C_{12}$-cycloalkyl radical, or an optionally substituted $C_7-C_{20}$-aralkyl radical and X is a —NCO—, —NH—$CO_2R^1$—, —NH-$CO_2R^2$— or —NHCOCl—group, and $R^1$ and $R^2$ can be the same or different and are a straight chain or branched $C_1-C_{20}$-alkyl radical or a $C_5-C_{12}$-cycloalkyl radical; as well as a process for their preparation.

The 2-(alkoxymethyl)-pentane-1,5-diurethanes or 2-(alkoxymethyl)-pentane-1,5-dicarbamic acid chlorides are suited for the preparation of 2-(alkoxymethyl)-pentane-1,5-diisocyanates, which in turn are used for the preparation of plastics using the polyisocyanate addition polymerization process.

DETAILED DESCRIPTION OF THE PREFERRED EMBODIMENT

The object of the present invention is to produce novel aliphatic diisocyanates, which are meaningful as intermediate products, particularly for the preparation of plastics using the polyisocyanate addition polymerization process. The novel aliphatic diisocyanates are economical to produce industrially, and possess advantages in processability when compared to the prior art.

This object is met with 2-(alkoxymethyl)-pentane1,5-diisocyanates having the structural formula:

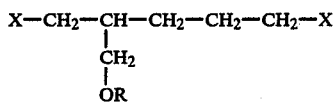

wherein R is:

a straight chain or branched $C_1-C_{20}$-alkyl radical, preferably a $C_1-C_{12}$-alkyl radical; or
a straight chain or branched $C_2-C_{20}$-alkenyl radical, preferably a $C_2-C_{12}$-alkenyl radical; or
a straight chain or branched $C_3-C_{20}$-oxaalkyl radical, preferably a $C_3-C_{12}$-oxaalkyl radical; or
an optionally substituted $C_5-C_{12}$-cycloalkyl radical, preferably an unsubstituted $C_6-C_{12}$-cycloalkyl radical or an optionally substituted $C_7-C_{20}$-aralkyl radical, or preferably an unsubstituted $C_7-C_{12}$-aralkyl radical.

Of particular interest are diisocyanates, having the structure of formula I, in which R is selected from the group consisting of methyl, ethyl, n-propyl, iso-propyl, n-butyl, iso-butyl, sec.-butyl, 2-methylbutyl, n-pentyl, neopentyl, 2-methylpentyl, n-hexyl, 2-ethylhexyl, n-octyl, n-decyl, n-dodecyl, cyclohexyl, benzyl, phenylethyl, methoxyethyl, ethoxyethyl, butoxyethyl and isobutoxyethyl, and mixtures thereof.

The most preferred compounds having the general structure of formula I are those selected from the group consisting of 2-(methoxymethyl)-pentane-1,5-diisocyanate, 2-(ethoxymethyl)-pentane-1,5-diisocyanate, 2-(n-propoxymethyl)-pentane-1,5-diisocyanate, 2-(iso-propoxymethyl)pentane-1,5-diisocyanate, 2-(n-butoxymethyl)-pentane-1,5-diisocyanate, 2-(2-methylbutoxymethyl)-pentane-1,5-diisocyanate, 2-(neopentoxymethyl)-pentane-1,5-diisocyanate, 2-(2-methylpentoxymethyl-pentane-1,5-diisocyanate, 2-(n-hexoxymethyl)-pentane-1,5-diisocyanate, 2-(2-ethylhexoxymethyl)-pentane-1,5-diisocyanate, 2-(n-dodecoxymethyl)-pentane-1,5-diisocyanate, 2-(n-cyclohexoxymethyl)-pentane-1,5-diisocyanate, 2-(2-methoxyethoxymethyl)-pentane-1,5-diisocyanate, 2-(2-ethoxyethoxymethyl)-pentane-1,5-diisocyanate, 2-(2-butoxyethoxymethyl)-pentane-1,5-diisocyanate, 2-(2-isobutoxythoxymethyl)-pentane-1,5-diisocyanate and mixtures thereof.

The 2-(alkoxymethyl)-pentane-1,5-diisocyanates which have the structure of formula I may be prepared by the thermal cleavage of 2-(alkoxymethyl)-pentane-1,5-diurethanes having the structure of formula II:

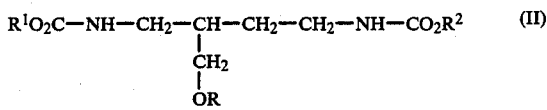

in which R possesses the aforesaid meaning and $R^1$ and $R^2$ are the same or are different and are a straight chain or branched $C_1-C_{20}$-alkyl radical, more preferably a $C_1-C_{10}$-alkyl radical, and most preferably a $C_3-C_6$-alkyl radical, or they are a $C_3-C_{15}$-cycloalkyl radical, more preferably a $C_5-C_{10}$-cycloalkyl radical, and most preferably a $C_5-C_8$-cycloalkyl radical.

Those skilled in the art will understand that the thermal cleavage of 2-alkoxymethyl-pentane-1,5-diurethanes may occur in the presence or absence of catalysts, under the following conditions:

(a) in the gas phase at temperatures in excess of 300° C. under reduced pressure or
(b) in the liquid phase at temperatures of from 175° to 350° C.

Compounds having the structure of formula I may also be prepared by the thermal cleavage of 2-(alkoxymethyl)-pentane-1,5-dicarbamic acid chlorides having the structure of formula III:

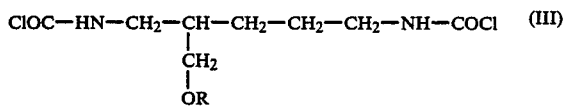

wherein R has the same meaning as in formula I. The thermal cleavage is carried out in the presence of inert organic solvents. Under the reaction conditions, the carbamate groups are thermally cleaved at temperatures ranging of about 80° to 200° C., and preferably of from about 120° to 200° C., to form the 2-(alkoxymethyl)-pentane-1,5-diisocyanates and hydrochloric acid.

The 2-(alkoxymethyl)-pentane-1,5-diurethanes having the structure of formula II and the 2-(alkoxymethyl)pentane-1,5-dicarbamic acid chlorides having the structure of formula III may be prepared by the reaction of 2-(alkoxymethyl)-pentane-1,5-diamines having the structure of formula IV:

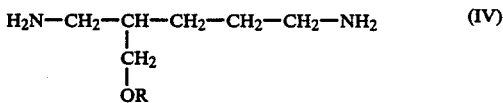

in which R has the aforesaid meaning, in the presence or absence of catalysts with urea and a primary and/or secondary alcohol R¹OH, respectively R²OH, whereby R¹ and R² have the aforesaid meanings, and optionally, in the presence of carbamic acid alkylesters and/or dialkylcarbonates. Optionally, the ammonia which is formed is separated.

Another method is by the phosgenation of 2-(alkoxymethyl)-pentane-1,5-diamines having the structure of formula IV or their salts, or preferably 2-(alkoxymethyl)-pentane-1,5-diaminhydrochlorides in a solvent or a diluent, to form the corresponding carbamic acid chloride, which is subjected to thermal cleavage to form the 2-(alkoxymethyl)pentane -1,5-diisocyanate of the present invention.

The novel 2-(alkoxymethyl)-pentane-1,5-diisocyanates of the present invention, as well as the starting materials 2-(alkoxymethyl)-pentane-1,5-dicarbamic acid chlorides and 2-(alkoxymethyl)-pentane-1,5-diurethanes may also be prepared in the following manner.

Specifically, 2-(alkoxymethyl)-pentane-1,5-diamines, as described by formula IV, are prepared by the hydrogenation, under increased temperature and pressure, and optionally in the presence of a catalyst, of a 2-(alkoxymethyl)-dinitriloglutarate having the structure of formula V:

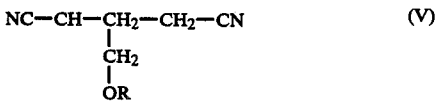

in which R has the aforesaid meaning, to produce the 2-(alkoxymethyl)pentane-1,5-diamines which are useful in the preparation of the novel diisocyanates of the present invention. They may also be produced according to the process disclosed in DE-A-No. 15 93 176 (GB-A-No. 1 097 360) in good yields from 2-methylenedinitriloglutarates and alcohol.

According to the preferred embodiment, 2-(alkoxymethyl)dinitriloglutarates having the structure of formula V are hydrogenated, optionally in an inert solvent, in the presence of hydrogen and ammonia at a temperature between about 50° and 200° C. in the presence of a hydrogenation catalyst using a metal selected from Group VIII from the Periodic Table, under a pressure of from about 1 to 300 bar.

The hydrogenation of 2-(alkoxymethyl)-dinitriloglutarates having the structure of formula V into 2-(alkoxymethyl)-pentane-1,5-diamines having the structure of formula IV can, theoretically, be conducted in a conventional fashion. For example, the hydrogenation may occur by catalytic hydrogenation by conversion with lithium aluminum hydride in an inert anhydrous solvent or using sodium in the presence of alcohols. However, it is preferred to utilize the catalytic hydrogenation process using catalysts from Group VIII of the Periodic Table to form the 2-(alkoxymethyl)-pentane-1,5-diamines which are useful for the preparation of the present invention.

As previously stated, the catalytic hydrogenation preferably takes place by heating a compound having the general structure of formula V in an inert solvent to a temperature of from about 50° to 200° C., preferably of from about 100° to 180° C., in the presence of hydrogen, ammonia and ordinary hydrogenation catalysts, preferably selected from Group VIII from the Periodic Table. Ammonia may be present stoichiometrically, but preferably, in excess. For example, the ammonia should be present in a mole ratio of from about 2:1 to 40:1 based on the dinitrile used, and, more preferably, in a mole ratio of from 5:1 to 25:1.

The reaction is carried out under a pressure of from about 1 to 300 bar, preferably of from about 50 to 180 bar of hydrogen.

Purification takes place in a conventional fashion such as by filtering off the catalyst, distillation and/or crystalization of the residue, or in any other manner known to those skilled in the art.

The reaction can be carried out in batches, or continuously. Suitable as reactors are, simple steel autoclaves, for continuous hydrogenation, and compression resistant steel pipes filled with packed bed catalyst or any other suitable reactor.

All common catalysts for nitrile hydrogenation are suitable as hydrogenation catalysts. It is preferred to use catalysts selected from Group VIII of the Periodic Table. Examples include nickel, cobalt, iron and mixtures thereof. Noble metal catalysts selected from the group consisting of palladium, platinum, ruthenium, rhodium, and mixtures thereof may also be used. The metal catalysts may be employed as solid catalysts in a fine distribution like Raney nickel or Raney cobalt suspension procedures, or as molded metal iron pigment catalysts, or as catalyst mixtures or deposited on carriers. Typical examples of carriers are aluminum oxide, silica gel, or magnesium silicate. Most preferred are Raney cobalt and iron pigment-catalysts.

In batch processing, the catalyst is employed in an amount of from about 1 to 100 weight percent and preferably of from about 10 to 50 weight percent, based on the amount of the compound to be used which has the general structure of formula V.

All inert solvents may be employed as solvents for the catalytic hydrogenation process. Preferred solvents may be selected from the group consisting of tetrahydrofuran, dioxane, and alcohols like methanol, ethanol, propanol or butanol, and mixtures of these. Even liquid ammonia is suited as a solvent. The solvent is used in an amount of from about 100 to 10,000 weight percent and preferably of from about 200 to 2000 weight percent, based on a starting component having the general structure of formula V.

Other methods are also suitable for nitrile hydrogenation. For example, nitrile hydrogenation may be conducted by reduction, using complex aluminum hydrides, (lithium aluminum hydride) in water-free inert solvents like ether or tetrahydrofuran, or by reduction with sodium in alcohols such as ethanol, propanol or n-butanol. Selection of the reduction method depends on the significance of the radical R in the compounds having the general structure of formula II: when R is an alkenyl, then catalytic hydrogenation is not as suitable as other processes, following the process described in German Patent No. DE-A-36 32 007.

The preferred 2-(alkoxymethy)-pentane-1,5-diamines having the structure of formula IV may also be prepared. The preferred 2-(alkoxymethyl)-pentane-1,5-diamines useful in the present invention are 2-(Methoxymethyl)-pentane-1,5-diamine, 2-(Ethoxymethyl)-pentane-1,5-diamine, 2-(n-Propoxymethyl)-pentane-1,5-diamine, 2-(Isopropoxymethyl)-pentane-1,5-diamine, 2-(n-Butoxymethyl)-pentane-1,5-diamine, 2-(2-Methylbutoxymethyl)-pentane-1,5-diamine, 2-(Neopentoxymethyl)-pentane-1,5-diamine, 2-(2-Methylpentoxymethylpentane-1,5-diamine, 2-(n-Hexoxymethyl)-pentane-1,5-diamine, 2-(2-Ethylhexoxymethyl)-pentane-1,5-diamine, 2-(n-Dodecoxymethyl)-pentane-1,5-diamine, 2-(n-Cyclohexoxymethyl)-pentane-1,5-diamine, 2-(2-Methoxyethoxymethyl)-pentane-1,5diamine, 2-(2-Ethoxyethoxymethyl)-pentane-1,5-diamine, 2-(2-Butoxyethoxymethyl)-pentane-1,5-diamine and, 2-(2-Isobutoxythoxymethyl)-pentane-1,5-diamine, and mixtures thereof.

In preparing 2-(alkoxymethyl)-pentane-1,5-dicarbamic acid chlorides having the general structure of formula III, 2-(alkoxymethyl)-pentane-1,5-diamines may be directly phosgenated or may be phosgenated as salts, and preferably as hydrochlorides, in solvents or diluents, using ordinary methods such as those known to persons of ordinary skill in the art. Typical solvents may be selected from the group consisting of toluene, xylene, chlorobenzene, dichlorobenzene, or mono- and-/or dicarboxylic esters having boiling points of from about 165° to 250° C., such as benzoic methylester, oxalic dimethylester and/or adipic dimethylester, and mixtures thereof. A solution of 2-(alkoxymethyl)-pentane-1,5-diamines or a suspension of the corresponding salts is then reacted at temperatures of from about 0° to 80° C. and preferably of from about 10° to 50° C., with from about 1 to 6 moles, more preferably of from 1 to 2.5 moles and most preferably of from 1 to 1.5 moles of phosgene per —NH$_2$—or—NH$_2$.HCl-group. The gaseous or liquid phosgene in this instance is added to the reaction mixture at a rate such that the gases exiting are predominately comprised of hydrogen chloride. By separating the solvent by distillation under normal or reduced pressure, or by any other method known in the art, the 2-(alkoxymethyl)-pentane-1,5-dicarbamic acid chlorides may be isolated and then purified using ordinary methods.

The 2-(alkoxymethyl)-pentane-1,5-dicarbamic acid chlorides formed from any of the above methods can be thermally cleaved to form 2-(alkoxymethyl)-pentane-1,5-diisocyanates and hydrogen chloride without intermediate isolation, in the presence of the aforementioned solvents at temperatures of from about 80° to 200° C., and preferably of from 120° to 180° C. After finishing the phosgenation and cleavage, the solvent is distilled off, preferably under reduced pressure, such as from about 100 to 5 mbar. Optionally the hydrogen chloride and excess phosgene present may be removed from the diisocyanate solution before the solvent is distilled off by use of an inert gas, such as nitrogen.

The crude 2-(alkoxymethyl)-pentane-1,5-diisocyanates may then be purified using ordinary methods such as by distillation under reduced pressure.

According to the preferred embodiment, the 2-(alkoxymethyl)-pentane-1,5-diurethanes having the general structure of formula II are prepared by the reaction of 2-(alkoxymethyl)-pentane-1,5-diamines having the general structure of formula IV with urea and a primary and/or secondary alcohol R$^1$OH preferably R$^2$OH in the presence of dicarbamic alkylesters and/or dialkylcarbonates and optionally by removing the ammonia which formed. The reactions may be carried out in the presence or absence of catalysts.

However, the diurethanes having the general structure of formula II may be prepared using other methods, such as by the reaction of diamines with carbamic alkylesters according to specification EP-A-No. 18 588, or using dialkylcarbonates, in the presence of alcohols, or by the reaction of diamines with chloroformic alkylesters.

In a preferred process for preparing 2-(alkoxymethyl)-pentane-1,5-diurethanes having the general structure of formula II, 2-(alkoxymethyl)-pentane-1,5-diamines having the general structure of formula IV are reacted with urea and an alcohol in a mole ratio of from 1:1.5 to 10:2 to 50, more preferably 1:2.0 to 2.5:4 to 20 and most preferably 1:2.0 to 2.3:4 to 10, in the absence or presence of catalysts, at reaction temperatures of from about 175° to 250° C., preferably of from about 180° to 230° C. The ammonia formed during the course of the reaction is immediately separated off. The reaction is primarily carried out using low boiling-point alcohols under pressure, whereby the pressure is adjusted so that the reaction mixture boils at the prescribed reaction temperature. As a function of the alcohol used, the pressure is commonly from about 0.1 to 60 bar, preferably of from about 1 to 40 bar. Under these reaction conditions, reaction times are usually from about 0.5 to 50 hours, and preferably from about 3 to 15 hours.

Theoretically, all optionally substituted primary and-/or secondary aliphatic and/or cycloaliphatic alcohols having the formula R$^1$OH and R$^2$OH, in which R$^1$ and R$^2$ may be the same or different, are suitable as alcohols. However, it is preferred to select alcohols having boiling points sufficiently different than the boiling point of the 2-(alkoxymethyl)-pentane-1,5-diisocyanates obtained by subsequent chemical cleavage, so that quantitative separation of the cleavage products, diisocyanate and alcohol, is possible and the 2-(alkoxymethyl)-pentane-1,5-diurethanes formed may be vaporized without decomposition.

Examples of R$^1$ and/or R$^2$OH alcohols are aliphatic, optionally substituted, primary or secondary alcohols having from about 1 to 20 carbon atoms, preferably from 1 to 10 carbon atoms, or most preferably from about 3 to 6 carbon atoms in a straight chain or branched alkyl radical and/or cycloaliphatic, optionally substituted alcohols having from about 3 to 15 carbon atoms and particularly from about 5 to 8 carbon atoms in an optionally substitued cycloalkyl radical. Typical examples of alcohols are: methanol, ethanol, propanol, 2-phenyl-propanol, n-butanol, isobutanol, 2- and 3-methylbutanol, neopentyl alcohol, pentanol, 2-methylpentanol, n-hexanol, 2-ethylhexanol, n-heptanol, n-octanol, n-nonanol, n-decanol, n-dodecanol, benzyl alcohol, isopropanol, sec. butanol, sec.-isoamyl alcohol, cyclopentanol, cyclohexanol, 2-, 3- or 4-methylcyclohexanol and tert.-butyl-cyclohexanol. Preferably used are: methanol, ethanol, n-propanol, n-butanol, iso-butanol, n-pentanol, iso-pentanol, n-hexanol or mixtures of aliphatic and/or cycloaliphatic alcohols as well as particularly n-propanol, n- and/or iso-butanol, and mixtures thereof.

As previously mentioned, the reaction of the 2-(alkoxymethyl)-pentane-1,5-diamines having the general structure of formula IV can be carried out with urea and alcohol in the presence of carbamic alkylesters and/or dialkylcarbonates. In the various processing variations, dialkylcarbonate is employed in an amount of from about 1 to 30 mole percent, preferably of from about 5 to 25 mole percent. It is also contemplated to use carbamic alkylester in an amount of from about 1 to 20 mole percent and preferably from about 5 to 18 mole percent, based on the mole percent of 2-(alkoxymethyl)-pentane-1,5-diamines used. However, it is preferred to use mixtures comprised of dialkylcarbonates and carbamic alkylesters in the said quantity ratios. The preferred dialkylcarbonates and/or carbamic alkylesters are those whose alkyl radicals correspond to the alkyl radical of the alcohol used.

Catalysts may be used to increase the rate of reaction for preparing 2-(alkoxymethyl)pentane-1,5-diurethanes having the general structure of formula II. The catalysts may be employed in catalytically effective amounts and are preferably employed in amounts of from about 0.1 to 20 weight percent, more preferably of from about 0.5 to 10 weight percent and most preferably of from about 1 to 5 weight percent based on the weight of the 2-(alkoxymethyl)pentane-1,5-diamines used. Inorganic or organic compounds which are suited as catalysts are those which contain one or more cations, and preferably a cation of a metal from the Groups IA, IB, IIA, IIB, IIIA, IIIB, IVA, IVB, VA, VB, VIB, VIIB and VIIIB of the Periodic Table, defined according to the *Handbook of Chemistry and Physics* 14th edition, published by Chemical Rubber Publishing Co., 23 Superior Ave. N.E., Cleveland, Ohio. Suitable organic and inorganic compounds suited as catalysts may be selected from the group consisting of halides like chlorides and bromides; sulfates, phosphates, nitrates, borates, alcoholates, phenolates, sulfonates, oxides, hydroxides, carboxylates, chelates, carbonates and thio- or dithiocarbamates and mixtures thereof. Typical examples of suitable cation catalysts may be selected from the group consisting of lithium, sodium, potassium, magnesium, calcium, aluminum, gallium, tin, lead, bismuth, antimony, copper, silver, gold, zinc, mercury, cerium, titanium, vanadium, chromium, molybdenum, manganese, iron, cobalt, nickel, and mixtures thereof. Preferably, cations of lithium, calcium, aluminum, tin, bismuth, antimony, copper, zinc, titanium, vanadium, chromium, molybdenum, manganese, iron cobalt, and mixtures thereof are used. The catalysts may be used even in the form of their hydroxides or ammonium compounds.

The following compounds are examples of typical catalysts: lithium methylate, lithium ethylate, lithium propylate, lithium butylate, sodium methylate, potassium tert.-butylate, magnesium methylate, calcium methylate, tin(II)chloride, tin-(IV)-chloride, lead acetate, lead phosphate, antimony-(III)-chloride, antimony-(V)-chloride, aluminum isobutylate, aluminum trichloride, bismuth-(III)-chloride, copper(II)-acetate, copper-(II)-sulfate, copper-(II)-nitrate, bis(triphenylphosphinoxydo)-copper-(II)-chloride, copper molybdate, silver acetate, gold acetate, zinc oxide, zinc chloride, zinc acetate, zinc acetonyl acetate, zinc octoate, zinc oxalate, zinc hexylate, zinc benzoate, zinc undecylate, cerium-(IV)-oxide, uranium acetate, titanium tetrabutylate, titanium tetrachloride, titanium tetraphenylate, titanium naphthylate, vanadium-(III)-chloride, vanadium acetonylate, chrome-(III)chloride, molybdenum-(VI)-oxide, molybdenumacetylacetonate, tungsten-(VI)-oxide, manganese-(II)-acetate, manganese-(III)acetate, iron-(II)-acetate, iron-(III)-acetate, iron phosphate, iron oxalate, iron-(III)-chloride, iron-(III)-bromide, cobalt acetate, cobalt chloride, cobalt sulfate, cobalt naphthanate, nickel chloride, nickel acetate and nickel naphthanate and mixtures thereof.

It is also advantageous to immediately remove the ammonia as it is formed from the reaction mixture by any method, i.e. by distillation. When distillation is employed to remove ammonia from the reaction mixture, it is conducted at temperatures from about 60° to 150° C., and preferably from about 65° to 120° C. In this manner, precipitation and deposition of amonium carbaminate, which forms in small quantities from ammonia and carbon dioxide by the decomposition of urea, is avoided.

After completing the reaction, the dialkylcarbonates and/or the carbamic alkylesters are removed from the reaction mixture and are stored to be reused in subsequent batches. However, in continuous processing they are returned directly to the beginning of the diurethane preparation process.

Separation of the compounds of the reaction can take place in one or more steps. It is preferred to use a two-stage process. In this instance, in the first stage the alcohol, which has a residual alcohol content of from about 1 to 30 weight percent, and preferably of from about 2 to 15 weight percent based on the weight of the reaction mixture, is distilled off and returned into the beginning of the process to form a concentrated reaction mixture.

In the second step, the concentrated reaction mixture, which is comprised predominately of 2-(alkoxymethyl)-pentane-1,5-diurethanes and may also contain 2-(alkoxymethyl)-pentane-1,5-oligourea-polyurethanes and even residual alcohol, dialkylcarbonate and/or dicarbamic alkylesters, is treated in a stripping column using from about 50 to 5000 liters, and preferably from about 100 to 1000 liters of inert gas per liter of concentrated reaction mixture, for about one hour at stripping temperatures of from about 50° to 200° C., preferably of from about 120° to 180° C., in order to completely separate substantially all of the residual alcohol, the dialkylcarbonates and/or the carbamic alkylesters. Suitable inert gases in this instance are for example, nitrogen, carbon monoxide, rare gases, natural gas and mixtures thereof. The low boiling-point compounds which are stripped off are then condensed, and optionally retained and stored to be reused in other batches. In continuous processing, they are preferably returned to the beginning of the diurethane preparation process.

From the reaction mixture obtained by distillation or preferably by stripping, which is essentially comprised of 2-(alkoxymethyl)-pentane-1,5-diurethanes having structure II and optionally 2-(alkoxymethyl)-pentane-oligourea polyurethanes, the 2-(alkoxymethyl)-pentane- 1,5-diurethanes may be isolated by ordinary methods such as by distillation, and then optionally be subjected to an additional purification process.

The reaction mixture which is comprised essentially of 2-(alkoxymethyl)-pentane-1,5-diurethanes and optionally 2-(alkoxymethyl)-pentane-oligourea-polyurethanes, is preferably thermally cleaved directly into the 2-(alkoxymethyl)pentane-1,5-diisocyanates having the general structure of formula I and an alcohol.

The thermal cleavage can be carried out in a conventional fashion such as in the gas stage at temperatures in excess of about 300° C. under reduced pressure in the absence of dissolved catalysts according to U.S. Pat. No. 3,870,739 (DE-A-No. 24 10 505) or in the presence of catalysts, according to DE-A-No. 19 44 719 (GB No. 1 247 451), or in the liquid phase, at temperatures of from about 175° to 350° C., preferably of from about 200° to 280° C. in tthe presence of catalyst-free solvents according to the specifications of U.S. Pat. Nos. 3,962,302 (DE-A-No. 24 21 503), or 3,919,280 (DE-A-No. 25 30 001) or in the presence of solvents and catalysts as disclosed in the specification of DE-A-No. 26 35 490.

The 2-(alkoxymethyl)-pentane-1,5-diurethane mixtures, which optionally contain small quantities of 2-(alkoxymethyl)pentane-oligourea polyurethanes, may be evaporated in a liquid or solid form or as a suspension or solution in an inert solvent, under the aforementioned reaction conditions, in an evaporator and then thermally cleaved in a subsequent thermal reactor.

In a preferred embodiment of this process, the solvent free diurethane mixture is introduced as a melt into the evaporator using a proportioning pump and heated to from about 80° to 180° C., preferably from 100° to 150° C.

Film-type evaporators or forced circulation evaporators, which operate at temperatures of from 200° to 300° C., more preferably from 220° to 300° C. and most preferably from 240° to 280° C. under a pressure of from 0.1 to 200 mbar, more preferably from 5 to 100 mbar, have proven particularly useful as evaporators. Indeed, any other evaporator can also be used, such as agitated-film evaporators, A.P. Reactors (manufactured by Krauss-Maffei), propeller calandri evaporators or wiped-film evaporators.

When using film-type evaporators it is also possible to evaporate the entire 2-(alkoxymethyl)-pentane-1,5-diurethane mixture. However, is is preferred that a portion of the diurethane mixture fed into the evaporator, together with the optionally present 2-(alkoxymethyl)pentane-oligourea-polyurethane, is discharged from the evaporator unevaporated as molten material, since in so doing, one achieves a significant cleaning effect on the baffles of the evaporator. The weight ratio of evaporated to unevaporated 2-(alkoxymethyl)pentane-1,5-diurethanes can vary within a wide range, and is from about 20:80 to 90:10. The melt discharged from the evaporator is preferably returned directly to the beginning of the diurethane preparation process, i.e., into the diurethane forming step.

The 2-(alkoxymethyl)-pentane-1,5-diurethane vapors are introduced into the thermal reactor at a temperature in excess of about 300° C., more preferably from about 310° to 480° C. and most preferably from about 350° to 450° C., under reduced pressure, such as from about 0.1 to 200 mbar, more preferably from about 0.1 to 100 mbar and most preferably from 1 to 50 mbar, and then thermally cleaved, either by a batch procedure or, preferably, continuously to form the 2-(alkoxymethyl)-pentane-1,5-diisocyanates having the general structure of formula I and an alcohol.

The thermal reactor is generally a tubular reactor and can have any given tube cross section. However, it is preferred to use longitudinal, cylinder type thermal reactors. The ratio of the inside diameter to the length of the thermal reactor is generally from about 1:2 to 1:1000, and preferably from about 1:10 to 1:500. The thermal reactor can be arranged either vertically or horizontally and can occupy adjoining buildings. The preferred reactors are thermal tubular reactors, in which the tubular inner diameter is about 10 to 100 millimeters and the length of the tubes are about 0.5 to 5.0 meters.

The cleavage may also be carried out in the presence of thermally stable reactor packed materials. Suitable as packing materials are temperature resistant and gas-permeable materials such as beads, wool, rings and/or turnings from carbon, steel, brass, copper, zinc, aluminum, titanium, chromium, cobalt, nickle, quartz and mixtures thereof. Several of these materials have proven preferred for use such as steel, brass, aluminum, zinc, and mixtures thereof, since they lead to better cleavage results. This better cleavage may be due to synergism due to the catalytic action and better heat transfer.

From the thermal reactor, the disassociation products, which are in the vapor phase and comprised almost exclusively of 2-(alkoxymethyl)-pentane-1,5-diisocyanates and alcohol, are fed into a multi-stage, preferably a two-stage, steam condensation device. In the first condensation step, which is conducted at a pressure of from about 0.1 to 100 mbar at temperatures of from about 60° to 120° C., the 2-(alkoxymethyl)-pentane-1,5-diisocyanates will almost completely condense out.

In the second condensation step, essentially only alcohol is condensed, which is then returned to the beginning of the diurethane preparation process for preparing the diurethanes. The temperature of the second condensation step is governed by the boiling point of the alcohol being condensed and by the system pressure, and is from about 5° to 30° C.

The 2-(alkoxymethyl)-pentane-1,5-diisocyanates having the general structure of formula I obtained from the first condensation step are generally subject to distillation to a purity of over about 99.5 weight percent. The sump product which results can optionally be returned to the beginning of the diurethane preparation process.

Depending on the selection of the condensation temperatures and as a function of the system pressure, alcohol in the first condensation step and diisocyanates in the second condensation step may be co-condensed in varying quantities. According to one of the preferred embodiments, in the second condensation step, co-condensed diisocyanate is reacted completely with excess alcohol into 2-(alkoxymethyl)-pentane-1,5-diurethanes. Following the separation of the alcohol, it is returned once again for evaporation and cleavage. However, it is also possible, according to another preferred embodiment, to return the diurethanes with the dialkylcarbonate and/or carbamic alkylesters to the beginning of the diurethane preparation process.

Similarly, during the first condensation step, co-condensed alcohol is allowed to react completely with excess diisocyanate. The reaction product, after distillation and separation of the diisocyanate, is subjected to evaporation and thermal cleavage. In a preferred embodiment, it is mixed with the alcohol obtained in the second condensation step and returned into the beginning of the diurethane preparation process.

The novel 2-(alkoxymethyl)-pentane-1,5-diisocyanates having the general structure of formula I are excellent starting materials for the preparation of polyurethane plastics, polyurea plastics, polyurethane-polyureaplastics. By using the polyisocyanate addition polymerization process, it is possible to form coatings, coating compounds, sealing compounds, adhesives, elastomers, fibers, floor coverings, cellular plastics, etc. By selecting the radical "R", physical properties such as boiling point, vapor pressure, polarity and solubility may be modified. Further, processing conditions may be adapted so that, optionally, the mechanical properties of the resulting plastics may be adjusted, varied and improved. The products are particularly suited for the preparation of light-resistant polyurethane coatings and polyurethane coating materials.

The novel 2-(alkoxymethyl)-pentane-1,5-diurethanes having the general structure of formula II are useful final products and intermediate products. They are also suitable for use as pest control agents. As intermediate products they can be employed as starting components for polycondensation systems, for example by the reaction with lower and/or higher polyhydroxyl compounds and/or polyamines, for preparing plastics or plastic fibers. Preferably they find application in the preparation of diisocyanates by thermal cleavage. The novel 2-(alkoxymethyl)-pentane-1,5-dicarbamic acid chlorides are especially suited for preparing diisocyanates.

The following examples are offered to illustrate various aspects of the invention. Those skilled in the art will understand that many variations are possible and the examples are not to be construed as limiting the scope and spirit of the invention.

EXAMPLE 1

In a stainless steel autoclave, 12.5 g of 2-(butoxymethyl)dinitriloglutarate, 70 ml of tetrahydrofuran and 10 g of Raney-cobalt were added under agitation. After forcing 50 ml of liquid ammonia into the mixture, the pressure was increased with hydrogen to 140 bar and the autoclave was heated to 110° C. By repressurising, the hydrogen pressure was maintained constant at 160 bar. After 10 hours at 110° C., it was cooled down, the pressure relieved, and the reaction batch was analyzed by gas chromatography. The yield of 2-(butoxymethyl)-pentane-1,5-diamine was, at a complete conversion, 85 percent of the theoretical. By fractional distillation, one obtained pure 2-(butoxymethyl)-pentane-1,5-diamine having a boiling point of from 84° to 86° C./0.3 mbar.

EXAMPLE 2

120 g of 2-(hexoxymethyl)-dinitriloglutarate, 900 ml of tetrahydrofuran and 70 g Raney cobalt were combined together in a stainless steel autoclave with 200 ml of liquid ammonia. While stirring and under a hydrogen blanket, it was heated for five hours to 110° C. and heated for ten hours to 120° C. By repressurizing with hydrogen, the pressure was maintained between 150 and 170 bar. Following cooling and releasing of the pressure, the reaction batch was analyzed by gas chromatography. The yield of 2-(hexoxymethyl)-pentane 1,5-diamine, at complete conversion, was 76 percent of the theoretical. By fractional distillation one obtained pure 2-(hexoxymethyl)-pentane-1,5-diamine having a boiling point of from 110° to 115° C./0.6 mm.

EXAMPLE 3

A tubular reactor was filled with 178 ml of an iron catalyst which was obtained by the reduction of iron oxides with hydrogen at a temperature of about 500° C., such as disclosed in DE-A No. 24 29 293. In a trickle bed procedure, 10 grams of 2-(butoxymethyl)-dinitriloglutarate, 90 grams of tetrahydrofuran, 6.5 grams of liquid ammonia, 10 liters of the crude hydrogenated mixture (a loop reactor) as well as hydrogen, were fed in hourly. The hydrogenation was carried out at a temperature of 160° C. and at a pressure of 100 bar. After evaporating the ammonia, the crude hydrogenated product was analyzed by gas chromatography. The yield of 2-(butoxymethyl)-pentane-1,5-diamine, based upon the reacted 2-(butoxymethyl-dinitriloglutarate was 74 percent of the theoretical yield.

EXAMPLE 4

91 g of 2-(2-methoxyethoxymethyl)-dinitriloglutarate, 800 ml tetrahydrofuran, 90 g Raney cobalt and 200 ml liquid ammonia were placed in a stainless steel autoclave and, while stirring and under a hydrogen blanket, were heated to 110° C. for five hours and then to 120° C. for ten hours. By repressurizing, the hydrogen pressure was maintained constant at 150 bar. After cooling and relieving the pressure, the reaction batch was analyzed by gas chromotography. The yield of 2-(2-methoxyethoxymethyl)-pentane-1,5-diamine , at complete conversion, was 68 percent of the theoretical yield. Fractional distillation produced pure 2-(2-methoxyethoxymethyl)-pentane-1,5-diamine, having a boiling point of 105° to 107° C./0.3 mbar.

EXAMPLE 5

In a one liter agitated autoclave fitted with a pressure column and a pressure regulating valve, 188.0 g of 2(butoxymethyl)-pentane-1,5-diamine, 126.0 g of urea and 370.0 g of butanol were heated for 4 hours at 230° C. and at a pressure of 9 bar to facilitate removing the ammonia on a reflex condenser. 609.0 g of a clear liquid was obtained, which indicated, by means of GPC, 95 percent conversion into 2-(butoxymethyl)-1,5-bis-(butoxycarbonylamnino)pentane. After distilling off the excess butanol and small quantities of carbamic butylester, the residue was 374.0 g of a viscous liquid, which was subjected to thermal cleavage without any further purification. Using column chromatography on silica gel, pure 2-(butoxymethyl)-1,5-bis(butoxycarbonylamino)-pentane, which was a colorless, viscous oil was obtained. The results of the chromotography are given below.

| C,H,N—Analysis: | C | H | N |
| --- | --- | --- | --- |
| calculated | 61.82% | 10.38% | 7.21% |
| actual | 62.04% | 10.19% | 7.34% |

EXAMPLE 6

A cleavage device, comprised of a film-type evaporator, a cleavage reactor (cylindrical pipe made from V2A-steel having a nominal volume of about 1 L equipped with galvanized metal packing material) and a two-stage steam condensation device, was evacuated to 5 mbar. 350 g of 2-(butoxymethyl)-1,5-bis(butoxycarbonylamino)-pentane obtained according to Example 5 was introduced into the film-type evaporator and heated to 260° C., whereby 315 g evaporated and 35 g was discharged. The diurethane vapors entered the cleavage reactor, which had an average temperature of 400° C. The cleavage gas which emerged was fractionally condensed in an adjoining two stage condensation device at 65° to 18° C. In the first condenser, 217 g of crude diisocyanate was formed, which was purified by vacuum distillation (transition temperature of from 130° to 132° C./0.3 mbar). 125.5 g (a 63 percent yield) of 2-(butoxymethyl)pentane-1,5-diisocyanate having a purity of 98 percent was obtained. The results are given below.

| C,H,N—Analysis: | C | H | N |
| --- | --- | --- | --- |
| calculated | 60.49% | 7.61% | 11.76% |
| found | 60.40% | 7.73% | 11.89% |

EXAMPLE 7

In a one liter agitated autoclave fitted with a pressure column and pressure regulating valve, 216 g of 2-(hexoxymethyl)pentane-1,5-diamine, 126 g of urea and 440 g of butanol were heated for five hours at 230° C. and 10 bar while removing the ammonia on a reflex condenser. 702 g of a clear liquid was obtained which, by means of a GPC analysis, indicated 97 percent conversion into 2-(hexoxymethyl)-1,5-bis(butoxycarbonylamino)-pentane. After distilling off the excess alcohol and small amounts of carbamic butylester, 398 g of a viscous liquid remained, which was used in a thermal cleavage without any further purification. By column chromatography on silica gel, pure 2-(butoxymethyl)-1,5-bis-(butoxy-carbonylamino)pentane which appeared as a colorless, viscous oil, was obtained. The results of chromatography are given below.

| C,H,N—Analysis: | C | H | N |
| --- | --- | --- | --- |
| calculated | 63.43% | 10.65% | 6.72% |
| actual | 63.48% | 10.78% | 6.60% |

EXAMPLE 8

Thermal cleavage was carried out in a device as described in Example 6. 550 g of 2-(hexoxymethyl)-1,5-bis(butoxycarbonylamino)-pentane, obtained in accordance with the procedure of Example 7, were introduced into a film-type evaporator which was heated to 280° C. and evacuated to from 8 to 9 mbar; whereby 509 g evaporated and 41 g was discharged. The temperature in the cleavage reactor was, on the average, 400° C. In the condenser, which operated at 85° C., 343 g of crude isocyanates was collected. This was preliminarily purified by distillation using a film-type evaporator (oil temperature 160° C./0.2 mbar) and once again distilled under reduced pressure at from 123° to 125° C./0.2 mbar. 207 g (a 65 percent yield) of 2-(hexoxymethyl)-pentane-1,5-diisocyanate having a purity of 99 percent was obtained. The results of mass spectrometry are given below:

| C,H,N—Analysis: | C | H | N |
| --- | --- | --- | --- |
| calculated | 63.13% | 8.33% | 10.52% |
| found | 63.20% | 8.41% | 10.33% |

EXAMPLE 9

In a one liter autoclave fitted with a pressure column and a pressure regulating valve, 190 g of 2-(2-methoxyethoxymethyl)-pentane-1,5-diamine, 126 g of urea and 440 g of butanol were added under agitation, and heated for six hours at 230° C. and at 10 bar while removing the ammonia on a relex condenser. 685 g of a clear, yellowish liquid was obtained, which by means of GPC analysis indicated 96 percent conversion into 2-(methoxyethoxymethyl)-1,5-bis(butoxycarbonylamino)-pentane. After distilling off the excess butanol and small amounts of carbamic butylester, 380 g of a viscous liquid remained, which was used in the thermal cleavage without any further purification.

By column chromatography on silica gel, one obtained pure 2-(2-methoxyethoxymethyl)-1,5-bis-(butoxycarbonylamino)-pentane as a colorless, viscous oil. The analysis was as follows:

| C,H,N—Analysis: | C | H | N |
| --- | --- | --- | --- |
| calculated | 60.93% | 10.23% | 7.48% |
| actual | 60.66% | 10.29% | 7.38% |

EXAMPLE 10

18.8 g of 2-(Butoxymethyl)-pentane-1,5-diamine was added dropwise to a mixture comprised of 200 g of o-dichlorobenzene and 60 g of phosgene, with vigorous stirring and with ice cooling to 0° C. After finishing the addition, the resulting suspension was heated to 130° C. At this temperature phosgene was added into the reaction mixture over the course of 2.5 hours. After cooling, the excess phosgene was expelled with a vigorous stream of nitrogen. The o-dichlorobenzene was distilled off under reduced pressure at 10 mbar and the residue was distilled at from 125° to 128° C. at 0.2 mbar. 18.7 g (a 78 percent yield) of 2-butoxymethyl-pentane-1,5-diisocyanate was obtained.

The embodiments of the invention in which an exclusive privilege or property is claimed are defined as follows:

1. An 2-(Alkoxymethyl)-pentane-1,5-diisocyanate, having the structural formula:

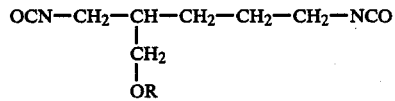

wherein
R is either
a straight chain or branched $C_1$–$C_{20}$ alkyl radical,
a straight chain or branched $C_2$–$C_{20}$ alkenyl radical,
a straight chain or branched $C_3$–$C_{20}$ oxaalkyl radical,
an optionally substituted $C_5$–$C_{12}$ cycloalkyl radical, or
an optionally substituted $C_7$–$C_{20}$ aralkyl radical.

2. An 2-(Alkoxymethyl)-pentane-1,5-diurethanes, having the structural formula:

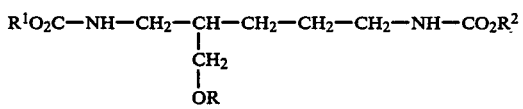

wherein
R is either
a straight chain or branched $C_1$–$C_{20}$ alkyl radical,
a straight chain or branched $C_2$–$C_{20}$ alkenyl radical,
a straight chain or branched $C_3$–$C_{20}$ oxaalkyl radical,
an optionally substituted $C_5$–$C_{12}$ cycloalkyl radical, or
an optionally substituted $C_2$–$C_{20}$ aralkyl radical, and $R^1$ and $R^2$, which may be the same or different, are either
a straight chain or branched $C_1$–$C_{20}$ alkyl radical or a $C_3$–$C_{15}$ cycloalkyl radical.

3. An 2-(Alkoxymethyl)-pentane-1,5-dicarbamic acid chloride, having the structural formula:

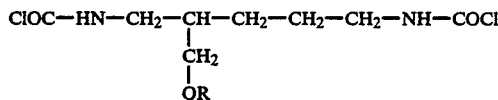

wherein
R is either
a straight chain or branched $C_1$–$C_{20}$ alkyl radical,
a straight chain or branched $C_2$–$C_{20}$ alkenyl radical,
a straight chain or branched $C_3$–$C_{20}$ oxaalkyl radical,
or an optionally substituted $C_5$–$C_{12}$ aralkyl radical.

4. A method for the preparation of an 2-(alkoxymethyl)-pentane-1,5-diisocyanate having the structural formula:

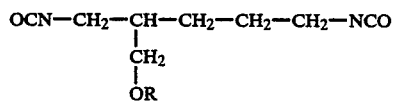

wherein
R is either
a straight chain or branched $C_1$–$C_{20}$ alkyl radical,
a straight chain or branched $C_2$–$C_{20}$ alkenyl radical,
a straight chain or branched $C_3$–$C_{20}$ oxaalkyl radical,
an optionally substituted $C_5$–$C_{12}$ cycloalkyl radical, or
an optionally substituted $C_2$–$C_{20}$ aralkyl radical, comprising thermally cleaving 2-(alkoxymethyl)pentane-1,5-diurethanes having the structural formula:

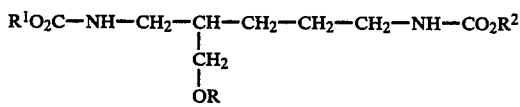

in which R has the above-stated meaning and $R^1$, and $R^2$ may be the same or different and are either a straight chain or branched $C_1$–$C_{20}$ alkyl radical or a $C_3$–$C_{15}$ cycloalkyl radical either
(a) in the gas phase at temperatures in excess of 300° C. under reduced pressure or
(b) in the liquid phase at temperatures from 175° to 350° C.

5. The method of claim 4, further including an catalyst, selected from the group consisting of cations of Group VIII of the Periodic Table.

6. A method for the preparation of an 2-(alkoxymethyl)-pentane-1,5-diisocyanate having the structural formula:

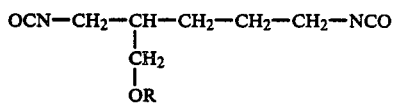

wherein
R is either
a straight chain or branched $C_1$–$C_{20}$ alkyl radical,
a straight chain or branched $C_2$–$C_{20}$ alkenyl radical,
a straight chain or branched $C_3$–$C_{20}$ oxaalkyl radical,
an optionally substituted $C_5$–$C_{12}$ cycloalkyl radical, or
an optionally substituted $C_7$–$C_{20}$ aralkyl radical, comprising thermally cleaving 2-(alkoxymethyl)-pentane-1,5-dicarbamic acid chloride having the structural formula:

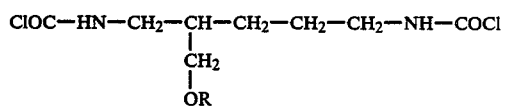

in which R has the above-stated meaning, in the presence of an inert, organic solvent at temperatures from 80° to 200° C.

7. A method for the preparation of an 2-(alkoxymethyl)-pentane-1,5-diurethane having the structural formula:

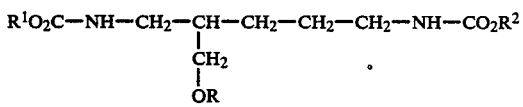

wherein
R is either
a straight chain or branched $C_1$–$C_{20}$ alkyl radical,
a straight chain or branched $C_2$–$C_{20}$ alkenyl radical,
a straight chain or branched $C_3$–$C_{20}$ oxaalkyl radical,
an optionally substituted $C_5$–$C_{12}$ cycloalkyl radical, or
an optionally substituted $C_7$–$C_{20}$ aralkyl radical, and $R^1$ and $R^2$, which may be the same or different, are either a straight chain or branched $C_1$–$C_{20}$ alkyl radical or a $C_3$–$C_{15}$ cyclo-alkyl radical, comprising reacting an 2-(alkoxymethyl)-pentane-1,5-diamine having the structural formula:

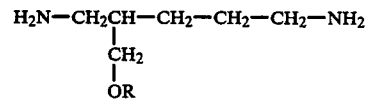

in which R has the above-stated meaning, with urea and a primary and/or secondary alcohol having the formula $R^1OH$ and/or $R^2OH$ respectively, whereby the radicals $R^1$ and $R^2$ have the above-stated meaning.

8. The method of claim 7, further including a reacting the 2-(alkoxymethyl)-pentane-1,5-diamine with urea and the primary and/or secondary alcohol in the presence of an carbamic acid alkyl ester and/or dialkyl carbonate.

9. The method of claim 7 further including a catalyst selected from Group VIII of the Periodic Table, and mixtures thereof.

10. The method of claim 7 further including removing ammonia as it is formed.

11. The method of claim 7, wherein the 2-(alkoxymethyl)-pentane-1,5-diamine is reacted with urea and alcohol in a mole ratio from about 1:1.5 to 10:2 to 50.

12. The method of the preparation of claim 8 wherein the carbamic acid alkyl ester corresponds to the alcohol is used, and is present in an amount from about 1 to 20 mole percent based on the 2-(alkoxymethyl)-pentane-1,5-diamine.

13. A plastic, formed via the polyisocyanate addition process, using the 2-(alkoxymethyl)-pentane-1,5-diisocyanate of claim 1.

14. A composition matter having the structural formula:

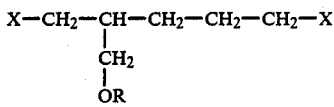

wherein
R is
a straight chain or branched $C_1$–$C_{20}$ alkyl radical; a straight chain or branched $C_2$–$C_{20}$ alkenyl radical, a straight chain or branched $C_3$–$C_{20}$ oxaalkyl radical; an optionally substituted $C_5$–$C_{12}$ cycloalkyl radical; or an optionally substituted $C_7$–$C_{20}$ aralkyl radical; and, X is an —NCO—, —NH—$CO_2R^1$—, —$NHCO_2R^2$— or —NHCOCl group, whereby $R^1$ and $R^2$ can be the same or different and are either a straight chain or branched $C_1$–$C_{20}$ alkyl radical or a $C_5$–$C_{12}$ cycloalkyl radical, said compositions of matter selected from the group consisting of 2-(alkoxymethyl)-pentane-1,5-diisocyanate, 2-(alkoxymethyl)-pentane-1,5-diurethane, 2-(alkoxymethyl)-pentane-1,5-dicarbamic acid chloride, and mixtures thereof.

* * * * *